United States Patent [19]

Horodysky et al.

[11] 4,446,037

[45] May 1, 1984

[54] FRICTION REDUCING ADDITIVES AND COMPOSITIONS THEREOF

[75] Inventors: Andrew G. Horodysky, Cherry Hill; Joan M. Kaminski, Clementon, both of N.J.

[73] Assignee: Mobil Oil Corporation, New York, N.Y.

[21] Appl. No.: 481,706

[22] Filed: Apr. 4, 1983

Related U.S. Application Data

[62] Division of Ser. No. 267,105, May 26, 1981.

[51] Int. Cl.³ .......................... C10M 1/32; C10M 1/38
[52] U.S. Cl. ....................................... 252/47.5; 44/71; 252/51.5 A
[58] Field of Search .......................... 252/47.5, 51.5 A; 44/71

[56] References Cited

U.S. PATENT DOCUMENTS

| | | | |
|---|---|---|---|
| 3,312,619 | 4/1967 | Dale | 252/47.5 |
| 3,697,574 | 10/1972 | Piasek et al. | 252/49.6 |
| 3,846,318 | 11/1974 | Lowe | 252/47.5 |
| 4,273,665 | 6/1981 | Horodysky et al. | 252/46.3 |
| 4,394,278 | 7/1983 | Horodysky et al. | 252/46.3 |

*Primary Examiner*—Jacqueline V. Howard
*Attorney, Agent, or Firm*—Alexander J. McKillop; Michael G. Gilman; Claude E. Setliff

[57] ABSTRACT

The invention provides (1) products of reaction formed by reacting a hydrolyzed imidazoline, a mercaptan and an aldehyde and (2) products of reaction of (1) and a boron compound, as well as lubricant compositions containing same.

19 Claims, No Drawings

FRICTION REDUCING ADDITIVES AND COMPOSITIONS THEREOF

This is a division of copending application Ser. No. 267,105, filed May 26, 1981.

BACKGROUND OF THE INVENTION

1. Field of the Invention

This invention relates to lubricant additives and compositions thereof and, more particularly, to liquid hydrocarbon fuel and lubricant compositions comprising fuels or oils of lubricating viscosity or greases prepared therefrom containing a minor friction reducing amount of products made by reacting together (1) substituted imidazolines, aldehydes and mercaptans or (2) the products thereof with boron compounds.

2. Description of the Prior Art

Many means have been employed to reduce overall friction in modern engines, particularly automobile engines. The primary reasons are to reduce engine wear thereby prolonging engine life and to reduce the amount of fuel consumed by the engine thereby reducing the engine's energy requirements or fuel consumption. While it is commonly understood that lubricants by definition, reduce friction between moving surfaces, friction reducing additives are agents which when added to lubricants in minor amounts significantly enhance the frictional properties of those lubricants without modifying other physical properties such as viscosity, density, pour point, and the like.

Many of the solutions to reducing fuel consumption have been strictly mechanical, as for example, setting the engines for a leaner burn or building smaller cars and smaller engines. However, considerable work has been with lubricating oils, mineral and synthetic, to enhance their friction or antioxidant properties by modifying them with friction reducing additives.

Although imidazolines have been added to lubricants for various purposes, the reaction products of this invention are, to applicants' best knowledge, novel, and they have no prior history of use in lubricating compositions as friction reducing additives or in the multifunctional additive areas of anti-corrosion, anti-wear or anti-oxidation. It is further understood that the borated derivatives of this invention possess multifunctional capabilities, i.e., anti-wear, anti-oxidation and/or bearing corrosion protection in addition to friction modification.

SUMMARY OF THE INVENTION

In accordance with the invention, there is provided a product of reaction produced by (1) reacting a hydrolyzed imidazoline with a mercaptan and an aldehyde, followed by (2) reacting the product of reaction of (1) with a boron compound. Also provided is a lubricant composition containing same.

DESCRIPTION OF SPECIFIC EMBODIMENTS

The imidazolines useful in this invention are fully or partially hydrolyzed products of 2-hydroxyalkyl-hydrocarbyl imidazolines, represented by structure I

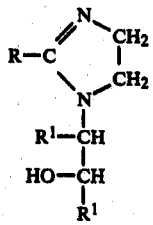

wherein R is alkyl, alkenyl, cycloalkyl, cycloalkenyl, alkaryl, aralkyl or aralkenyl containing from 9 to about 29 carbon atoms and $R^1$ is hydrogen or an alkyl group containing from 1 to about 6 carbon atoms. The aryl ring component can contain from 6 to 14 carbon atoms.

The hydrolyzed imidazolines of the invention may be prepared by reaction of the aforementioned imidazoline with water optionally in the presence of a catalyst and a solvent such as an alcohol, e.g., ethanol. Representative hydrolysis products are depicted by structures II and III below:

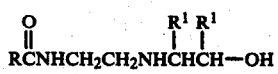

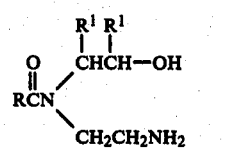

wherein R and $R^1$ are as defined under formula I.

A stoichiometric amount of water, or as much as a 4 mole excess, can be used. The reaction solvent can be any suitable low boiling alcohol, such as ethanol or butanol. Although an acid catalyst such as hydrochloric acid or acetic acid can be used for the hydrolysis reaction, the imidazoline will nevertheless hydrolyze in the absence of any catalyst. The reaction time can vary from 1 to 6 hours, with a preferred reaction time of 3 hours. The temperature of reaction can range from about 70° to about 120° C., preferably about 90° C.

The Mannich base is prepared by reacting hydrolyzed imidazoline with an aldehyde of the formula

wherein $R^2$ is H or a $C_1$ to $C_8$ hydrocarbyl group (e.g., alkyl, alkenyl, alkaryl or aralkyl) and a mercaptan of the formula

wherein $R^3$ is a $C_4$ to $C_{18}$ hydrocarbyl group, preferably an alkyl group.

The useful aldehydes, of which formaldehyde and paraformaldehyde are preferred, include acetaldehyde, propionaldehyde, butyroaldehyde and 2-ethylhexyl aldehyde.

Preferred among the mercaptans is n-dodecyl mercaptan. Others that may be used include n-hexyl, n-octyl, n-decyl, n-myristyl, n-hexadecyl, and n-oleyl mercaptan.

The following equation depicts the structure of a product that may be present, at least to some extent, in the Mannich base.

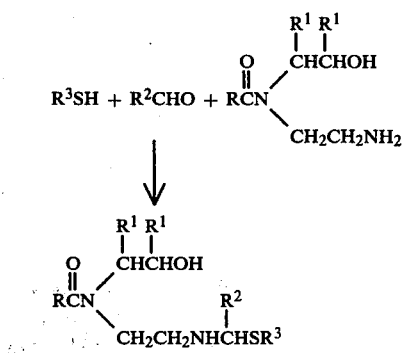

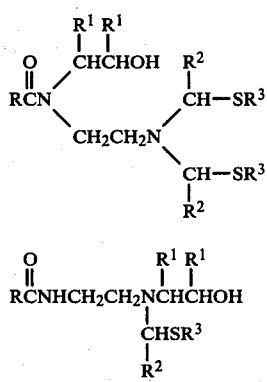

It is likely that a variety of other compounds are possible. These may include those of the following formulas:

$$\underset{RCN}{\overset{O}{\|}}\diagdown\underset{CH_2CH_2N}{\overset{\overset{R^1\ R^1}{|\ \ |}}{CHCHOH}}\diagdown\underset{\underset{R^2}{|}}{\overset{R^2}{CH-SR^3}}$$

$$\underset{RCNHCH_2CH_2NCHCHOH}{\overset{O\ \ \ \ \ \ \ \ \ \ \ \ \ \ \ R^1\ R^1}{\|\ \ \ \ \ \ \ \ \ \ \ \ \ \ \ |\ \ |}}$$
$$\overset{|}{\underset{R^2}{CHSR^3}}$$

For this reason, the compounds will be referred to herein as "reaction products" or "products of reaction" or an equivalent expression.

Mannich bases can be prepared by refluxing hydrolyzed imidazoline, aldehyde, and mercaptan at a ratio molar of from about 1:1:0.5 to about 1:1:1, respectively, in either polar or non-polar solvents such as n-butanol, isopropanol, toluene, or benzene until an expected amount of H₂O is removed. A temperature of from about 90° C. to about 60° C. can be used but from about 110° C. to about 140° C. is preferred.

Alternatively, the Mannich base can be prepared by reacting equimolar amounts of hydrolyzed imidazoline and aldehyde in the same solvents as above until an expected amount of H₂O is removed. The reaction is run for about 1 to 4 hours between about 90° and 145° C. Then, an equimolar amount, for example, of mercaptan may be added and reacted for about 3 to 6 hours at from about 120° C. to about 150° C.

The boron compound reactants have the following formula:

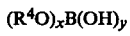
(R⁴O)ₓB(OH)_y wherein R⁴ is a C₁ to C₆ alkyl group, x is 0 to 3 and y is 0 to 3, wherein x+y is 3. R⁴ includes methyl, ethyl, propyl and butyl groups, preferably the latter. The preferred boron reactants are boric acid and tributyl borate. Boration is carried out with about 0.3 to about 2 equivalents of boron reactant, preferably in butanol or toluene for about 3 to 6 hours or until H₂O no longer distills over a temperature of from about 100° C. to 180° C., preferably about 110° C. to 160° C., is used. In view of the even more complex nature of this product, it will also be referred to as a product of reaction.

Some of the possible products are shown as follows:

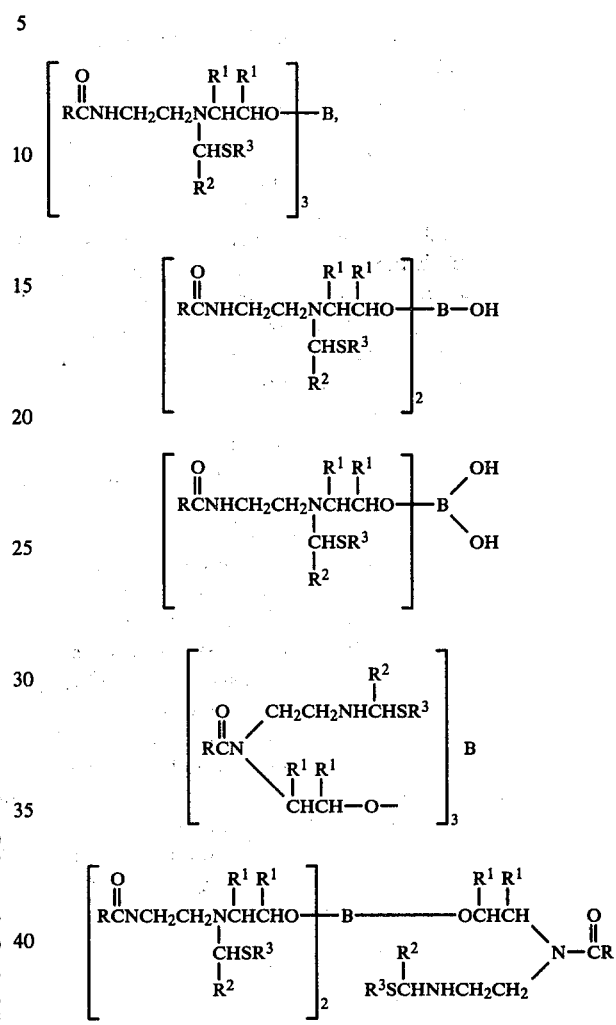

In general, in most instances, the product (either the Mannich base or the borated product thereof) is employed in an amount from about 0.1% to about 10% by weight, and preferably in an amount of from about 0.5% to about 5% by weight of the total weight of the composition. When used in fuels, they may be present to the extent of from about 0.00001 to about 1% by weight, preferably from about 0.001 to about 0.01% by weight.

Of particular significance, is the ability to counteract the accelerating effect of oxidation on metal and lubricant deterioration achieved by employing the aforementioned product. These products may be incorporated in lubricating media which may comprise liquid hydrocarbon oils in the form of either a mineral oil or a synthetic oil, or in the form of a grease, in which any of the aforementioned oils are employed as a vehicle. These lubricants can also contain detergents and dispersants, as well as inhibitors, antiwear, extreme pressure, antifoam, pour depressant, and viscosity index improving additives without negating the beneficial properties of the novel compositions of this invention. In general, mineral oils employed as the lubricant or grease vehicle may be of any suitable lubricating viscosity range as, for example, from about 45 SSU at 100° F. to about 6,000 SSU at 100° F., and preferably from about 50 SSU at 210° F. to about 250 SSU at 210° F. These oils may have viscosity indexes varying from below 0 to about 100 or higher. Viscosity indexes from about 70 to about 95 are preferred. The average molecular weights of these oils may range from about 250 to 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, di(-butylphthalate) fluorocarbons, silicate esters, silanes, esters of phosphorous-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl) ether, phenoxy phenylethers, etc.

The lubricating vehicles of the aforementioned greases of the present invention, containing the above-described products, are combined with a grease-forming quantity of a thickening agent. For this purpose, a wide variety of material may be employed. These thickening or gelling agents may include any of the conventional metal salts or soaps, which are dispersed in the lubricating vehicle in grease-forming quantities, in such degree as to impart to the resulting grease composition the desired consistency. Other thickening agents that may be employed in the grease formation may comprise the non-soap thickeners, such as surface modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for forming greases, can be used in preparing the aforementioned improved greases in accordance with the present invention.

The following Examples will specifically illustrate the invention. It will be understood that they are meant to be illustrations of and not limitations to the invention.

EXAMPLE 1

Ring-opening hydrolysis of 1-(2-hydroxyethyl)-2-heptadecenyl imidazoline

A mixture of 1-(2-hydroxyethyl)-2-heptadecenyl imidazoline (4798 g), water (1125 g), ethanol (1160 g) and glacial acetic acid (48 g) was stirred and heated at 90° C. for 3 hours. The water and ethanol were removed by high speed rotary evaporation. The resulting product was a golden waxy solid. The infrared spectrum of the product contained a strong carbonyl absorption band in the 1640–1650 cm$^{-1}$ region and showed no characteristic imidazoline carbon-nitrogen imido band at 1600 cm$^{-1}$, indicating complete ring-opening of the starting imidazoline.

EXAMPLE 2

Mannich reaction of hydrolyzed 1-(2-hydroxyethyl)-2-heptadecenyl imidazoline

Approximately 100 g of hydrolyzed 1-(2-hydroxyethyl)-2-heptadecenyl imidazoline (prepared as described in Example 1), 8.58 g of formaldehyde, and 55 g of a n-dodecyl mercaptan were refluxed in 200 cc toluene until the expected amount of water had been removed by azeotropic distillation. The reaction temperature was raised from 115° C. to 135° C., and no additional water formed. Toluene was removed by high speed rotary evaporation, and the residue was filtered through diatomaceous earth. The infrared spectrum of the clear, reddish-brown fluid product contained no characteristic imidazoline carbon-nitrogen imido band at 1600 cm$^{-1}$. Therefore, no recyclization had occurred.

EXAMPLE 3

Boration of the Mannich reaction product of hydrolyzed 1-(2-hydroxyethyl)-2-heptadecenyl imidazoline Approximately 100 g of the Mannich reaction product of hydrolyzed 1-(2-hydroxyethyl)-2-heptadecenyl imidazoline (prepared as described in Example 2), 7.0 g of boric acid, and 100 cc of toluene were refluxed and water was removed until water was no longer formed in the reaction. The reaction temperature was raised from 110° C. to 163° C. as the reaction proceeded. Toluene was removed by high speed rotary evaporation. The residue was filtered through diatomaceous earth to yield a dark brown viscous fluid.

EVALUATION OF THE PRODUCTS

The Mannich base derived from the reaction of 1-(2-hydroxyethyl)-2-heptadecenyl imidazoline, formaldehyde, and mercaptan and its borated derivatives were blended into a fully formulated engine oil (SAE 5W-20) containing an inhibitor package which includes detergent and dispersant and tested on the Low Velocity Friction Apparatus (LVFA).

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12–13 ml. of test lubricant are placed on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant.

Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The data are percent decrease in friction according to:

$$\frac{(U_k \text{ of oil alone}) - (U_k \text{ of oil plus additive})}{(U_k \text{ of oil alone})} \times 100$$

Thus, the value for the oil alone would be zero for the form of the data used in the Table below.

TABLE I

| | Friction Characteristics | |
|---|---|---|
| | Additive Conc. | Reduction or % Change in Coefficient of Friction |
| Example No. | Wt. % | 5 Ft./Min. | 30 Ft./Min. |
| Base Oil | — | 0 | 0 |
| 2 | 4 | 22 | 17 |
| 3 | 4 | 41 | 29 |
| | 2 | 35 | 26 |
| | 1 | 23 | 22 |

From the the data it can readily be seen that friction was reduced significantly relative to the base oil with reduction of 41% in the coefficient of friction. Even with the use of only 1% of the borated derivative (see Example 3), the coefficient of friction was reduced by 23%.

The products were also evaluated for oxidation stability. In most cases, improvements in oxidative stability over the base oil were observed. Basically, the test lubricant is subjected to a stream of air which is bubbled through at the rate of 5 liters per hour at 425° F. for 24 hours. Present in the composition are samples of metals commonly used in engine construction, namely, iron, copper, aluminum, and lead. See U.S. Pat. No. 3,682,980, incorporated herein by reference, for further details of the test. Improvements in viscosity index or neutralization number (or both) show effective control. See results in Table 2.

TABLE 2

| | Catalytic Oxidation Test 40 hours @ 325° F. | | | |
|---|---|---|---|---|
| | Additive Conc. Wt. % | Lead Loss mg. | % Inc. in Visc. of Oxidized Oil Using KV @ 210° F. | Neutral Number NN |
| Base Oil - 0% Additive 200" Solvent Paraffin Neutral Lubricating Oil | — | −1.2 | 67 | 3.62 |

TABLE 2-continued

| | Catalytic Oxidation Test 40 hours @ 325° F. | | | |
|---|---|---|---|---|
| | Additive Conc. Wt. % | Lead Loss mg. | % Inc. in Visc. of Oxidized Oil Using KV @ 210° F. | Neutral Number NN |
| Example 2 | 1 | −0.42 | 23 | 5.31 |
| Example 3 | 1 | −1.1 | 11 | 1.49 |

Also, copper strip corrosion tests were run in accordance with ASTM D130-80, the results of which are shown in Table 3. Effective corrosion inhibition was observed.

TABLE 3

| | Copper Strip Corrosivity Characteristics | | |
|---|---|---|---|
| | Conc. in 200" SPN | ASTM D130-80 250° F., 3 Hrs. | ASTM D130-80 210° F., 6 Hrs. |
| Example 2 | 3 | 1B | 1B |
| | 1 | 1B | 1B |
| Example 3 | 3 | 1B | 1B |
| | 1 | 1B | 1B |

We claim:

1. A reaction product made by reacting hydrolyzed imidazoline with an aldehyde and a mercaptan, using a molar ratio of from about 1:1:05 to about 1:1:1, respectively, the reaction taking place at from about 110° C. to about 150° C.

2. The reaction product of claim 1 wherein the hydrolyzed imidazoline has one of the formulas

and

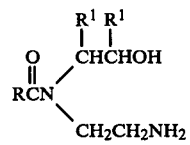

wherein R is a hydrocarbyl group containing from 9 to 29 carbon atoms and $R^1$ is hydrogen or a $C_1$ to $C_6$ alkyl group.

3. The reaction product of claim 1 wherein the mercaptan has the formula

wherein $R^3$ is a hydrocarbyl group containing from 4 to 18 carbon atoms.

4. The reaction product of claim 3 wherein the aldehyde has the formula

wherein $R^2$ is hydrogen or a $C_1$ to $C_8$ hydrocarbyl group.

5. The reaction product of claim 4 wherein the hydrocarbyl group of R is alkyl, alkenyl, alkaryl, aralkyl, cycloalkyl or cycloalkenyl.

6. The reaction product of claim 3 wherein $R^3$ is an alkyl group.

7. The reaction product of claim 1 made by reacting hydrolyzed hydrocarbyl 1-(2-hydroxyethyl)-2-heptadecenyl imidazoline, formaldehyde and n-dodecyl mercaptan.

8. A lubricant or liquid hydrocarbon fuel composition comprising a major proportion of a lubricant or fuel and an antifriction or antioxidant amount of a product made by reacting hydrolyzed imidazoline with an aldehyde and a mercaptan, using a molar ratio of from about 1:1:05 to about 1:1:1, respectively, the reaction taking place at from about 110° C. to about 150° C.

9. The composition of claim 8 wherein the imidazoline has one of the formulas

and

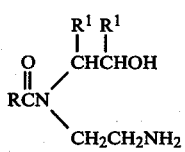

wherein R is a hydrocarbyl group containing from 9 to 29 carbon atoms and $R^1$ is hydrogen or a $C_1$ to $C_6$ alkyl group.

10. The composition of claim 8 wherein the mercaptan has the formula $R^3SH$ wherein $R^3$ is a hydrocarbyl group containing from 4 to 18 carbon atoms.

11. The composition of claim 10 wherein the aldehyde has the formula $R^2CHO$ wherein $R^2$ is hydrogen or a $C_1$ to $C_8$ alkyl group.

12. The composition of claim 11 wherein the hydrocarbyl group of R is alkyl, alkenyl, alkaryl, aralkyl, cycloalkyl or cycloalkenyl.

13. The composition of claim 10 wherein $R^3$ is an alkyl group.

14. The composition of claim 8 wherein the reaction product is made by by reacting hydrolyzed hydrocarbyl 1-(2-hydroxyethyl)-2-heptadecenyl imidazoline, formaldehyde and n-dodecyl mercaptan.

15. The composition of claim 8 wherein the lubricant is a lubricating oil.

16. The composition of claim 8 wherein the lubricant is a grease.

17. The composition of claim 15 wherein the lubricating oil is mineral oil.

18. The composition of claim 15 wherein the lubricating oil is a synthetic oil.

19. The composition of claim 15 wherein the lubricating oil is a mixture of mineral and synthetic oil.

* * * * *

UNITED STATES PATENT AND TRADEMARK OFFICE
CERTIFICATE OF CORRECTION

PATENT NO. : 4,446,037
DATED : May 1, 1984
INVENTOR(S) : Andrew G. Horodysky and Joan M. Kaminski It is certified that error appears in the above—identified patent and that said Letters Patent is hereby corrected as shown below:

Column 4, line 39, change "$RCNCH_2CH_2NCHCHO$" to --$RCNHCH_2CH_2NCHCHO$--

Signed and Sealed this

Twenty-third Day of October 1984

[SEAL]

Attest:

GERALD J. MOSSINGHOFF

Attesting Officer

Commissioner of Patents and Trademarks